United States Patent [19]

Hamaoka et al.

[11] 4,264,720

[45] Apr. 28, 1981

[54] COLOR PHOTOGRAPHIC LIGHT-SENSITIVE MATERIAL

[75] Inventors: Tsutomu Hamaoka; Masakazu Morigaki; Satoru Sawada; Nobutaka Ohki; Kotaro Nakamura, all of Minami-ashigara, Japan

[73] Assignee: Fuji Photo Film Co., Ltd., Minami-ashigara, Japan

[21] Appl. No.: 108,091

[22] Filed: Dec. 28, 1979

[30] Foreign Application Priority Data

Dec. 28, 1978 [JP] Japan ................................. 53/165358

[51] Int. Cl.$^3$ .......................... G03C 1/40; G03C 7/00
[52] U.S. Cl. .................................... 430/549; 430/551; 430/554; 430/555
[58] Field of Search ............... 430/551, 372, 554, 555, 430/549

[56] References Cited

U.S. PATENT DOCUMENTS

| | | | |
|---|---|---|---|
| 3,591,381 | 7/1971 | Gray et al. | 430/372 |
| 3,764,337 | 10/1973 | Arai et al. | 430/551 |
| 4,113,495 | 9/1978 | Shishido et al. | 430/551 |

Primary Examiner—J. Travis Brown
Attorney, Agent, or Firm—Sughrue, Rothwell, Mion, Zinn and Macpeak

[57] ABSTRACT

A silver halide color photographic light-sensitive material which contains a 3-anilino-5-pyrazolone type of magenta coupler and a novel dye image-stabilizing agent of the general formula (I) as hereinafter defined.

8 Claims, No Drawings

COLOR PHOTOGRAPHIC LIGHT-SENSITIVE MATERIAL

BACKGROUND OF THE INVENTION

1. Field of the Invention

The present invention relates to a color photographic light-sensitive material and, more particularly, to preventing discoloration of dye images and uncolored areas (herein referred to as "white areas") which are obtained after all processings including a development processing are finished.

2. Description of the Prior Art

Colored images obtained by subjecting silver halide color photographic light-sensitive materials to photographic processing are generally made up of azomethine dyes or indoaniline dyes which are formed by the reaction of couplers with the oxidation products of aromatic primary amine developing agents. Color photographic images so produced are stored or displayed as records for a long period of time. These photographic images are, however, not always stable to light, moisture and heat. Therefore, prolonged exposure to light or storage under high temperature and humidity usually cause fading or discoloration of the dye images and additionally discoloration in white areas to result in reduced image quality.

Such fading and discoloration are a serious disadvantage of recording materials. For the purpose of removing this disadvantage, compounds such as hydroquinone derivatives including 2,5-di-tert-butylhydroquinone, etc., phenol compounds such as 2,6-di-tert-butyl-p-cresol, 4,4'-methylenebis(2,6-di-tert-butylphenol), 2,2'-methylenebis-(4-ethyl-6-tert-butylphenyl), 4,4,'-isopropylidenediphenol, etc., tocopherol, and so on have been conventionally emmployed. These compounds undoubtedly prevent dye images from fading and discoloring, but some compounds have little effect as such and other compounds, which can contribute to prevent fading to a desirable extent, deteriorate hue, generate fog, or produce poor dispersions or crystallize. Thus, a color image stabilizing agent which can exhibit excellent effects upon photographic materials from an esthetic point of view has not been found among these compounds.

SUMMARY OF THE INVENTION

Therefore, an object of the present invention is to provide a color photographic light-sensitive material in which color images are stabilized by a particular color image-stabilizing agent, which can contribute satisfactorily to the prevention of fading and the discoloration of color images without an accompanying deterioration in hue and generation of fog.

The above-described object of the present invention is achieved by incorporating at least one compound represented by the following formula (I) into a photographic layer of a color photographic light-sensitive material:

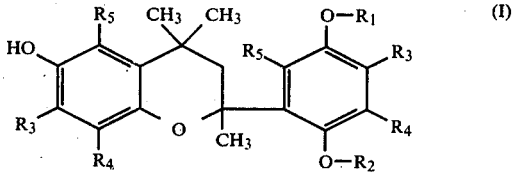

wherein $R_1$ and $R_2$ each represents a hydrogen atom, an alkyl group, a heterocyclic group, a trialkylsilyl group, an alkanesulfonyl group, a substituted or unsubstituted arylsulfonyl group, an aralkanesulfonyl group or a

group where Y represents an alkyl group, a substituted or unsubstituted aryl group, an aralkyl group, an alkoxy group, a substituted or unsubstituted aryloxy group, an aralkyloxy group, an alkylamino group, a dialkylamino group, a substituted or unsubstituted arylamino group, a diarylamino group, an alkyloxycarbonyl group, a substituted or unsubstituted aryloxycarbonyl group, an aralkyloxycarbonyl group or an acyl group, and $R_1$ and $R_2$ may be the same or different but cannot be hydrogen atoms at the same time; and $R_3$, $R_4$ and $R_5$ each represents a hydrogen atom, an alkyl group, an alkoxy group, a substituted or unsubstituted aryl group, a substituted or unsubstituted aryloxy group, an aralkyl group, an aralkoxy group, an alkenyl group, an alkenoxy group, an acylamino group, a halogen atom, an alkylthio group, a substituted or unsubstituted arylthio group, a diacylamino group, a substituted or unsubstituted acyl group, a sulfonamido group, an alkyl-amino group, an alkoxycarbonyl group or an acyloxy group, and $R_3$, $R_4$ and $R_5$ may be the same or different but cannot be hydrogen atoms at the same time.

DETAILED DESCRIPTION OF THE INVENTION

The color image stabilizing agent of the present invention is described below in greater detail.

$R_1$ and $R_2$, respectively, in the formula (I) represent a hydrogen atom, a straight chain, a branched chain or a cyclic alkyl group having 1 to 20 carbon atoms (e.g., methyl, ethyl, isopropyl, t-butyl, n-octyl, t-octyl, dodecyl, hexadecyl, cyclohexyl, etc.), a heterocyclic group and preferably 5- or 6-membered heterocyclic group having at least one hetero atom such as an oxygen atom, a nitrogen atom and a sulfur atom (e.g., tetrahydropyranyl, etc.), a trialkylsilyl group wherein the alkyl moieties preferably have 1 to 20 carbon atoms (e.g., trimethylsilyl, etc.), a straight chain, a branched chain or a cyclic alkanesulfonyl group having 1 to 20 carbon atoms (e.g., methanesulfonyl, propanesulfonyl, t-octanesulfonyl, octadecanesulfonyl, cyclohexanesulfonyl, etc.), a substituted or unsubstituted arylsulfonyl group wherein the aryl group is a mono- or bicyclic aryl group having a total of 6 to 30 carbon atoms including substituents (e.g., benzenesulfonyl, α-naphthalenesulfonyl, p-chlorobenzenesulfonyl, p-methoxybenzenesulfonyl, o-methylbenzenesulfonyl, etc.) or an aralkanesulfonyl group wherein the aralkyl moiety contains a mono- or bicyclic aryl group and preferably has a total of 7 to 30 carbon atoms including substituents (e.g., benzylsulfonyl, β-phenethylsulfonyl, etc.). $R_1$ and $R_2$ are preferably alkyl groups.

Y in a

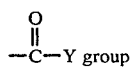 group represented by $R_1$ or $R_2$ includes a straight chain, a branched chain or a cyclic alkyl group having 1 to 20 carbon atoms (e.g., methyl, tert-butyl, cyclohexyl, tert-octyl, dodecyl, octadecyl, β-acetylaminopropyl, etc.), a substituted or unsubstituted aryl group and preferably a mono- or bicyclic aryl group having a total of 6 to 30 carbon atoms including substituents (e.g., phenyl, p-methylphenyl, p-methoxyphenyl, m-nitrophenyl, o-chlorophenyl, α-naphthyl, etc.), an aralkyl group wherein the aralkyl moiety contains a mono-or bicyclic aryl group and preferably has a total of 7 to 30 carbon atoms including substituents (e.g., benzyl, phenethyl, etc.), a straight chain, a branched chain or a cyclic alkoxy group having preferably 1 to 20 carbon atoms (e.g., methoxy, tert-butoxy, cyclohexyloxy, β-benzenesulfonyl ethyloxy, dodecyloxy, octadecyloxy, etc.), a substituted or unsubstituted aryloxy group wherein the aryl group is a mono- or bicyclic aryl group having a total of 6 to 30 carbon atoms including substituents (e.g., phenoxy, p-methylphenoxy, p-methoxyphenoxy, p-isopropylphenoxy, m-nitrophenoxy, 2,4,6-trichlorophenoxy, o-chlorophenoxy, α-naphthyloxy, β-naphthyloxy, etc.), an aralkyloxy group wherein the aralkyl moiety contains a mono- or bicyclic aryl group and preferably has a total of 7 to 30 carbon atoms including substituents (e.g., benzyloxy, phenethyloxy, etc.), an alkylamino or a dialkylamino group having 1 to 20 carbon atoms (e.g., methylamino, ethylamino, diethylamino, octadecylamino, dioctylamino, etc.), a substituted or unsubstituted arylamino or diarylamino group wherein the aryl group is a mono- or bicyclic aryl group having a total of 6 to 30 carbon atoms including substituents (e.g., phenylamino, p-methylphenylamino, p-nitrophenylamino, N,N-diphenylamino, α-naphthylamino, etc.), a straight chain, a branched chain or a cyclic alkyloxycarbonyl group having 1 to 20 carbon atoms (e.g., methoxycarbonyl, tert-butoxycarbonyl, cyclohexyloxycarbonyl, octyloxycarbonyl, etc.), a substituted or unsubstituted aryloxycarbonyl group and preferably a mono- or bicyclic aryloxycarbonyl group having 7 to 30 carbon atoms (e.g., phenoxycarbonyl, p-methylphenoxycarbonyl, p-methoxyphenyloxycarbonyl, m-nitrophenoxycarbonyl, o-chlorophenoxycarbonyl, etc.) or an aralkyloxycarbonyl group and preferably a mono- or bicyclic aralkyloxycarbonyl group having 8 to 30 carbon atoms (e.g., benzyloxycarbonyl, phenethyloxycarbonyl, etc.).

$R_3$, $R_4$ and $R_5$, respectively, in the formula (I) represent a hydrogen atom, a straight chain, a branched chain or a cyclic alkyl group having preferably 1 to 20 carbon atoms (e.g., methyl, tert-butyl, cyclopentyl, cyclohexyl, octyl, tert-octyl, tert-amyl, dodecyl, octadecyl, etc.), a straight chain, a branched chain or a cyclic alkoxy group having preferably 1 to 20 carbon atoms (e.g., methoxy, tert-butoxy, cyclohexyloxy, dodecyloxy, octadecyloxy, etc.), a substituted or unsubstituted aryl group wherein the aryl group is a mono- or bicyclic aryl group having a total of 6 to 30 carbon atoms including substituents (e.g., phenyl, p-methylphenyl, p-methoxyphenyl, p-octaneamidophenyl, o-chlorophenyl, o-methylphenyl, m-nitrophenyl, α-naphthyl, etc.), a substituted or unsubstituted aryloxy group wherein the aryl group is a mono- or bicyclic aryl group having a total of 6 to 30 carbon atoms including substituents (e.g., phenoxy, α-naphthoxy, p-methylphenoxy, p-methoxyphenoxy, p-caproamidophenoxy, o-chlorophenoxy, m-nitrophenoxy, etc.), an aralkyl group wherein the aralkyl moiety contains a mono- or bicyclic aryl group and preferably has a total of 7 to 30 carbon atoms including substituents (e.g., benzyl, phenethyl, etc.), an aralkoxy group wherein the aralkyl moiety contains a mono- or bicyclic aryl group and preferably has a total of 7 to 30 carbon atoms including substituents (e.g., benzyloxy, phenethyloxy, etc.), an alkenyl group and preferably a straight chain, branched chain or cyclic alkenyl group having 3 to 20 carbon atoms (e.g., allyl, etc.), an alkenoxy group and preferably a straight chain, branched chain or cyclic alkenoxy group having 3 to 20 carbon atoms (e.g., alloxy, etc.), an acylamino group (e.g., acetylamino, benzoylamino, caproamino, etc.), a halogen atom (e.g., chlorine, etc.), an alkylthio group whose alkyl moiety contains 1 to 20 carbon atoms and has a branched chain, a straight chain or a cyclic form (e.g., methylthio, tert-butylthio, hexylthio, cyclohexylthio, octadecylthio, etc.), a substituted or unsubstituted arylthio group and preferably a mono- or bicyclic arylthio group having 6 to 30 carbon atoms (e.g., phenylthio, p-methylphenylthio, o-carboxyphenylthio, o-methylphenylthio, o-methoxycarbonylphenylthio, m-nitrophenylthio, etc.), an aliphatic or aromatic diacylamino group having preferably 3 to 20 carbon atoms (e.g., succinimido, 3-hydantoinyl, etc.), a substituted or unsubstituted aliphatic or aromatic acyl group having 1 to 20 carbon atoms (e.g., acetyl, capryl, p-methoxybenzoyl, etc.), an alkyl- or arylsulfonamido group having 1 to 20 carbon atoms (e.g., methanesulfonamido, benzenesulfonamido, etc.), an alkylamino group whose alkyl moiety has 1 to 20 carbon atoms and has a branched or straight chain form (e.g., ethylamino, tert-butylamino, dioctylamino, octadecylamino, etc.), a branched or straight chain alkoxycarbonyl group having 1 to 20 carbon atoms (e.g., methoxycarbonyl, tert-butoxycarbonyl, octadecylcarbonyl, etc.) or an aliphatic or aromatic acyloxy group having 1 to 20 carbon atoms (e.g., acetoxy, caproxy, lauroxy, benzoyloxy, etc.). $R_3$, $R_4$ and $R_5$ are preferably an alkyl group or an alkoxy group.

Representative examples of compounds represented by the formula (I) are illustrated below. However, the compounds employed in the present invention are not to be construed as being limited to these examples.

Compound (1)

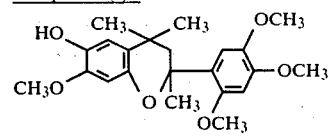

Compound (2)

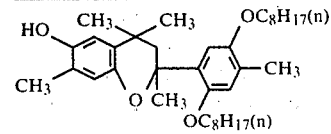

Compound (3)

-continued
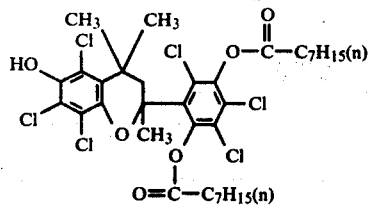
Compound (4)
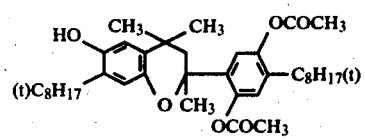
Compound (5)
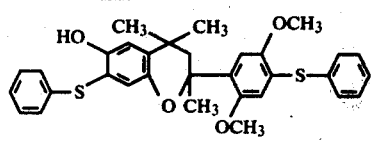
Compound (6)
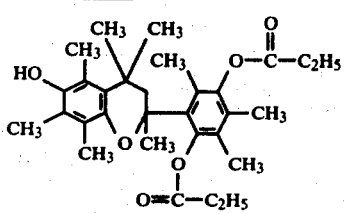
Compound (7)
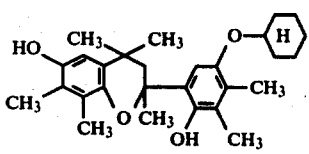
Compound (8)
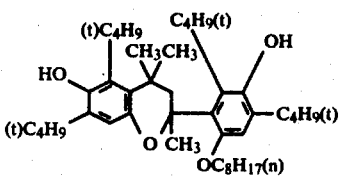
Compound (9)
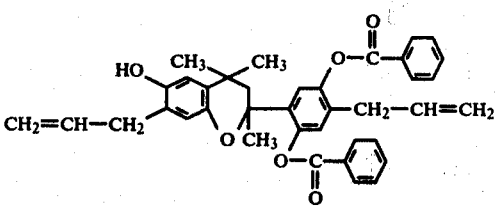
Compound (10)
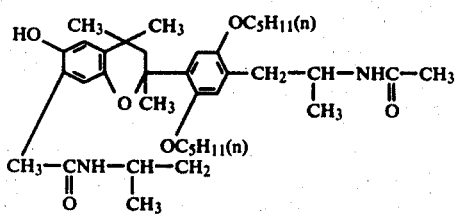
Compound (11)
-continued
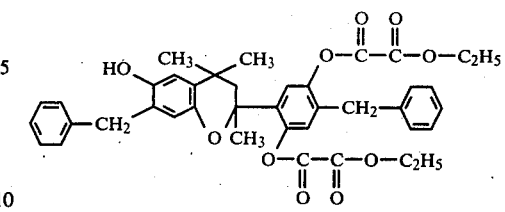
Compound (12)
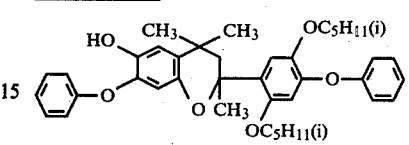
Compound (13)
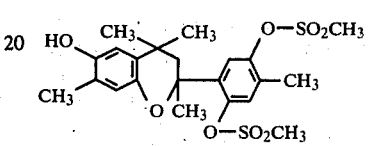
Compound (14)
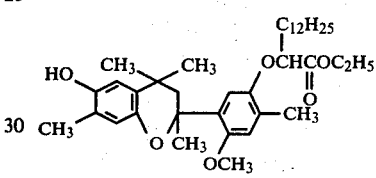
Compound (15)
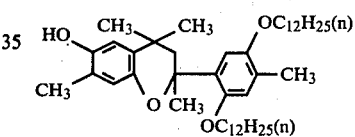
Compound (16)
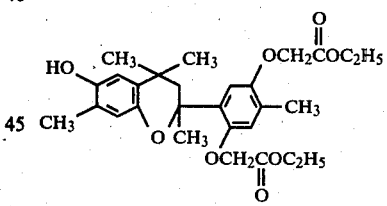
Compound (17)
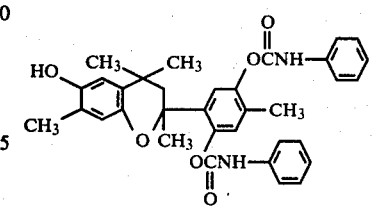
Compound (18)
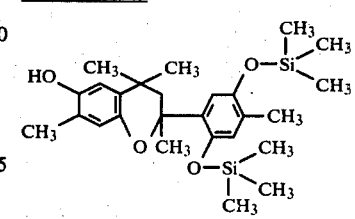
Compound (19)

-continued

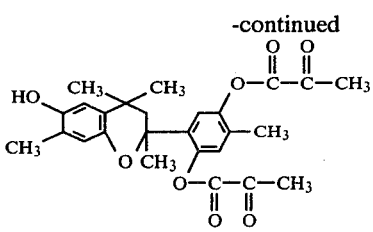

Compound (20)

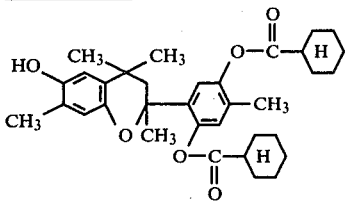

The compounds of the present invention can be obtained by being synthesized using 2-(2,5-dihydroxyphenyl)-6-hydroxy-2,4,4-trimethylchroman compounds, which are obtained by the method described in Japanese Patent Application (OPI) Ser. No. 152225/77 (The term "OPI" as used herein refers to a "published unexamined Japanese patent application"). Specifically, 2-(2,5-dihydroxyphenyl)-6-hydroxy-2,4,4-trimethylchroman compounds are synthesized by reacting a hydroquinone having substituents corresponding to $R_3$, $R_4$ and $R_5$ in the formula (I) with acetone using acetic acid and concentrated HCl as catalysts at room temperature for a suitable period of time as illustrated in Synthesis Example 1.

SYNTHESIS EXAMPLE 1

Synthesis of 2-(2,5-dihydroxy-4-methylphenyl)-6-hydroxy-2,4,4,7-tetramethylchroman 310 g of toluhydroquinone and 435 g of acetone were dissolved in a mixture of 850 ml of concentrated hydrochloric acid and 1,500 ml of glacial acetic acid and the resulting solution was stored for 16 days at 20 to 30° C. Precipitated crystals were separated by filtration and then recrystallized from methanol to obtain 100 g of a colorless crystal having a melting point of 190° C.

| Elemental Analysis for $C_{20}H_{24}O_4$ (%): | | |
| --- | --- | --- |
|  | C | H |
| Calculated: | 73.17 | 7.31 |
| Found: | 73.25 | 7.53 |

The synthesis of the compound of the present invention from 2-(2,5-dihydroxyphenyl)-6-hydroxy-2,4,4-trimethylchroman compounds is illustrated in Synthesis Example 2.

SYNTHESIS EXAMPLE 2

Synthesis of Compound (2)

98 g 2-(2,5-dihydroxy-4-methylphenyl)-6-hydroxy-2,4,4,7-tetramethylchroman and 100 g manganese dioxide were added to 400 ml of acetone, and were refluxed with continued heating and stirring for a period of approximately 3 hours. After separating manganese dioxide from the reaction product by filtration, the residue was washed with acetone. The solvent was distilled from the filtrate, and the residue was washed with methanol. After drying, 79 g of reddish-brown crystal of 6-hydroxy-2,4,4,7-tetramethyl-2-(4-methyl-2,5-benzoquinonyl)chroman was obtained. The melting point of the crystal was 203°–205° C.

| Elemental Analysis for $C_{20}H_{22}O_4$ (%): | | |
| --- | --- | --- |
|  | C | H |
| Calculated: | 73.60 | 6.80 |
| Found: | 73.53 | 6.84 |

70 g of 6-hydroxy-2,4,4,7-tetramethyl-2-(4-methyl-2,5-benzoquinonyl)chroman was added to 145 g of 2,3-dihydropyrane and thereto several drops of concentrated HCl was added. Thereafter, it was stirred at a temperature of 50° C. for 2 hours. After neutalization, 50 ml of ethanol was added to the reaction mixture and then it was cooled with ice cold water. To the resulting solution, 2.2 g of sodium borohydride dissolved in 80 ml of ethanol was added dropwise spending 1 hour in a stream of nitrogen. After the conclusion of the reaction, water was added to the reaction product and the product was extracted with ethyl acetate and dried with anhydrous sodium sulfate. After the removal of the solvent by distillation, the residue was purified using column chromatography to yield 58 g of pale yellow crystals of 2-(2,5-dihydroxy-4-methyl)-2,4,4,7-tetramethyl-6-(2-tetrahydropyranyloxy)chroman. The melting point of the product was 170°–172° C.

| Elemental Analysis for $C_{25}H_{32}O_5$ (%): | | |
| --- | --- | --- |
|  | C | H |
| Calculated: | 72.79 | 7.82 |
| Found: | 72.65 | 7.30 |

2-(2,5-dihydroxy-4-methyl)-2,4,4,7-tetramethyl-6-(2-tetrahydropyranyloxy)chroman and n-octylbromide were added in amounts of 50 g and 70 g, respectively, to 200 ml of ethanol and thereto 20 g of potassium hydroxide dissolved in 20 ml of water was added additionally in a stream of nitrogen. The mixture was refluxed with continued heating for a period of 6 hours. The resulting mixture was neutralized with an aqueous solution of hydrochoric acid. The salt precipitated by the neutralizing treatment was filtered and thereto were added 20 ml of water and 5 ml of concentrated HCl. This was refluxed with continued heating for a period of 4 hours. After conclusion of the reaction, water was added to the reaction product. The product was extracted with ethyl acetate and dried with anhydrous sodium sulfate. After the removal of the solvent by distillation, the residue was purified using column chromatography to yield 46 g of a pale yellow crystal. The crystal was recrystallized from methanol to result in the production of Compound (2) having a melting point of 78°–79° C.

| Elemental Analysis for $C_{36}H_{56}O_4$ (%): | | |
| --- | --- | --- |
|  | C | H |
| Calculated: | 78.21 | 10.21 |
| Found: | 78.34 | 10.39 |

The compounds employed in the present invention have very high solubilities to high boiling point solvents such as dibutyl phthalate, tricresyl phosphate and the like, which are commonly employed as solvents for dispersion into photographic emulsions. Therefore, they do not separate out during storage.

The compounds of the present invention do not cause fog and can prevent both the discoloration of magenta dye images and color changes in white areas from occurring, it may be concluded that the compounds of the present invention can exhibit aesthetically their excellent color image-stabilizing effects in photographic materials.

While the amount of the compound of the present invention depends upon the kind of coupler used in combination therewith, generally the compound is used in an amount of about 0.5 to 200% by weight based on the total amount of 3-anilino-5-pyrazolone magenta coupler used and preferably about 2 to 150% by weight. If the compound of the present invention is added in an amount below the above-described range, it has very little effect upon the prevention of discoloration in color image areas or the prevention of coloration in white areas, and such amounts are inadequate for practical uses. On the other hand, excess amounts are liable to hinder the progress of development and, consequently, lower color density.

In practicing the present invention, known fading inhibitors also can be used in combination with the compounds of the present invention. Known fading inhibitors may be used independently or in combinations of two or more. Specific examples of known fading inhibitors include phenol compounds such as 2,6-di-tert-butylphenol derivatives, gallic acid derivatives, p-alkoxyphenol derivatives, bisphenol derivatives, o-hydroxybenzylamine derivatives, aminophenol derivatives and the like; hydroquinone derivatives; $\alpha$-tocopherol derivatives (as described in U.S. Pat. No. 2,360,290); 5-hydroxychroman derivatives (as described in U.S. Pat. No. 3,573,050); 6-hydroxychroman derivatives (as described in U.S. Pat. No. 3,432,300); 6,6'-dihydroxy-4,4,4',4'-tetramethyl-2,2'-spirochroman derivatives (as described in U.S. Pat. No. 2,764,337); and so on.

3-anilino-5-pyrazolone type magenta couplers which may be effectively used in the present invention include as typical examples the compounds represented by the following general formula (II):

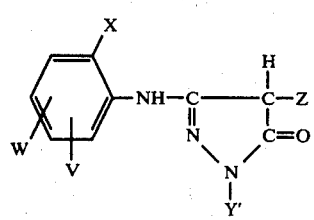

(II)

wherein X represents a straight chain, a branched chain or a cyclic alkyl group (e.g., methyl, ethyl, tert-butyl, cyclohexyl, octyl, dodecyl, etc.), a substituted or unsubstituted aryl group (e.g., phenyl, tollyl, etc.), an alkoxy group whose alkyl moiety may have a straight chain, a branched chain or a cyclic form (e.g., methoxy, ethoxy, isopropoxy, cyclohexyloxy, octyloxy, etc.), a substituted or unsubstituted aryloxy group (e.g., phenoxy, p-tert-butylphenoxy, naphthoxy, etc.), an N-substituted amino group (e.g., methylamino, diethylamino, anilino, etc.), an amido group (e.g., acetamido, butylamido, methylsulfonamido, diacylamido, etc.), a halogen atom (e.g., fluorine, chlorine, bromine, etc.), a hydroxy group, a cyano group or a nitro group; Y' represents a substituted or unsubstituted aryl group (e.g., phenyl, 2-chlorophenyl, 4-chlorophenyl, 2,5-dichlorophenyl, 2,6-dichlorophenyl, 2,4,6-trichlorophenyl, 2-bromophenyl, 3,5-dibromophenyl, 2-cyanophenyl, 4-cyanophenyl, 3-nitrophenyl, 4-nitrophenyl, 4-methylphenyl, 2,6-dimethylphenyl, 2,6-diethylphenyl, 4-butylphenyl, 2-trifluoromethylphenyl, 2-ethoxyphenyl, 2-phenylphenyl, 4-phenylphenyl, 4-phenoxyphenyl, 2-chloro-5-cyanophenyl, 5-chloro-2-methylphenyl, 2,6-dichloro-4-methylphenyl, 2-chloro-4,6-dimethylphenyl, 2,6-dichloro-4-methoxyphenyl, 2,6-dichloro-4-nitrophenyl, 2,4,6-trimethyl-3-nitrophenyl, 2,4,6-trimethyl-3-acetoamidophenyl, etc.) or a 5- or 6-membered heterocyclic group (e.g., 2-thiazolyl, 2-benzothiazolyl, 2-benzoxazolyl, 2-oxazolyl, 2-imidazolyl, 2-benzimidazolyl, etc.) and preferably Y' represents

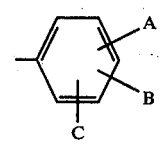

were A, B and C are the same or different and represent a hydrogen atom, a bromine atom, a chlorine atom, a cyano group, a methyl group or an alkoxy group; and W represents a hydrophobic ballast group, which should contain 4 to 35 (more particularly 8 to 32) carbon atoms in order to impart diffusion resistance to the coupler and is attached to the aromatic nuclear moiety of the anilino group directly or through an imino, an ether, a carbonamido, a sulfonamido, a ureido, an ester, an imido, a carbamoyl or a sulfamoyl bonding.

Some of specific examples of the ballast group are illustrated in detail below:

(i) Alkyl and alkenyl groups

For example, $-CH_2-CH(C_2H_5)_2$, $-C_{12}H_{25}$, $-C_{16}H_{33}$ and $-C_{17}H_{33}$.

(ii) Alkoxyalkyl groups

For example, $-(CH_2)_3-O-(CH_2)_7CH_3$ and $-(CH_2)_3OCH_2-\underset{\underset{C_2H_5}{|}}{CH}-(CH_2)_8-CH_3$, as described in Japanese Patent Publication No. 27563/64.

(iii) Alkylaryl groups

For example,

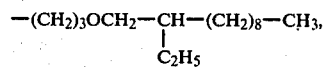

(iv) Alkylaryloxyalkyl groups

For example,

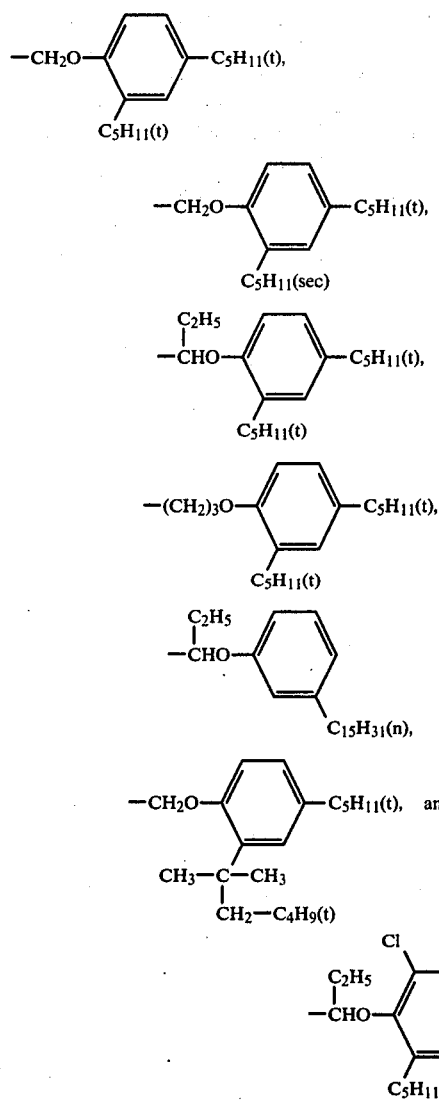

(v) Acylamidoalkyl groups

For example,

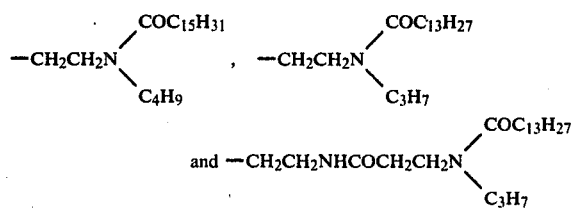

as described in U.S. Pat. Nos. 3,337,344 and 3,418,129.

(vi) Alkoxyaryl and aryloxyaryl groups

For example,

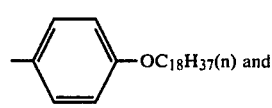

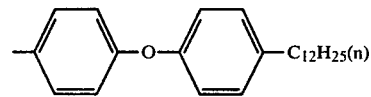

(vii) Residues having both a long chain alkyl or alkenyl moiety and a moiety capable of rendering them soluble in water, i.e., a carboxyl or sulfo group For example,

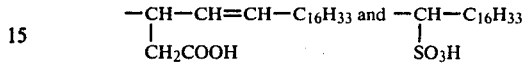

(viii) Alkyl groups substituted with ester groups

For example,

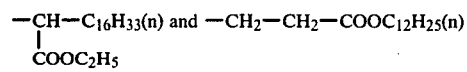

(ix) Alkyl groups substituted with aryl or heterocyclic groups

For example,

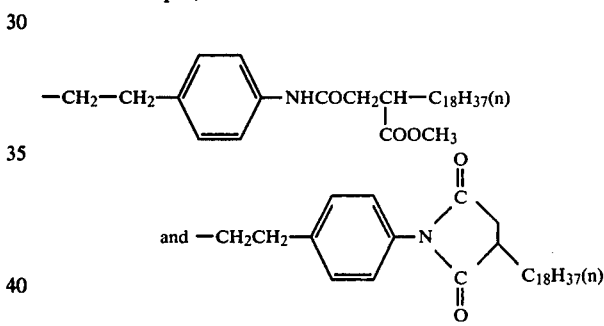

(x) Aryl groups substituted with aryloxyalkoxycarbonyl group

For example,

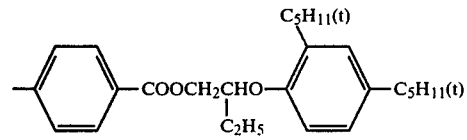

V in the general formula (II) represents a hydrogen atom or one of the groups defined as groups representing the above-described X or W. Z in the general formula (II) represents a hydrogen atom or a group capable of being elminated from the coupler upon the coupling reaction with an oxidized aromatic primary amine color developing agent, that is to say, a thiocyano group, an acyloxy group (e.g., acetoxy, dodecanoyloxy, octadecanoyloxy, 3-pentadecylphenoxy, benzoyloxy, β-naphthoyloxy, 3-[γ-(2,4-di-tert-amylphenoxy)-butylamido]benzoyloxy, etc.), an aryloxy group (e.g., phenoxy, p-chlorophenoxy, p-nitrophenoxy, naphthoxy, etc.), an aralkyloxycarbonyl group (e.g., benzyloxycarbonyl, etc.), an alkyloxycarbonyloxy group (e.g., ethyloxycarbonyloxy, etc.), a halogen atom (e.g., chlorine, fluorine etc.), a cycloalkoxy group (e.g., cyclohexyloxy, etc.), an aromatic amino group (e.g., phthalimido, etc.), a heterocyclic amino group (e.g., piperidino, etc.) or so on. Also, examples of other groups represented by Z may include such groups as bound to the coupling sites of the so-called colored couplers described in U.S. Pat. Nos. 2,455,170, 2,688,539, 2,725,292, 2,983,608 and 2,005,712, British Pat. Nos. 800,262 and 1,044,778, etc.; such groups as bound to the coupling sites of so-called development inhibitor releasing type (abbreviated DIR) couplers described in U.S. Pat. Nos. 3,148,062, 3,227,554 and 3,617,291, etc.; and such groups as bound to the coupling sites of the couplers described in U.S. Pat. Nos. 3,006,759, 3,214,437, 3,311,476 and 3,419,391, etc.

Specific examples of 3-anilino-5-pyrazolone type magenta couplers which are useful in the present invention are illustrated below. However, the present invention is not to be construed as being limited to these examples.

Coupler (A)

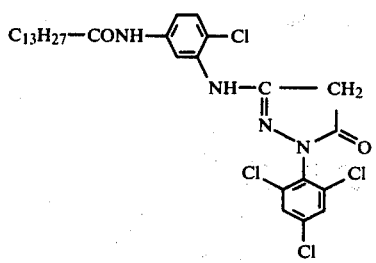

Coupler (B)

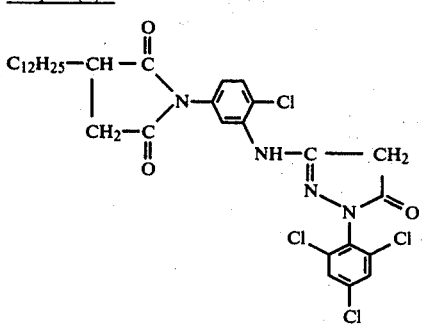

Coupler (C)

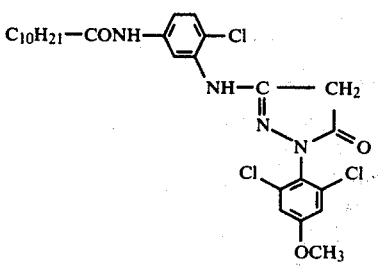

Coupler (D)

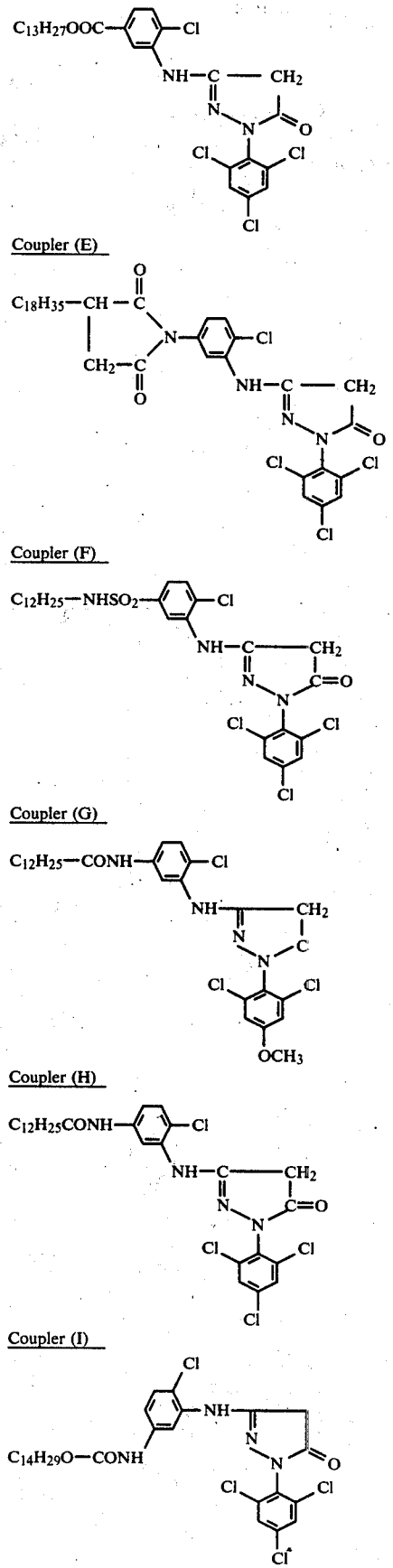

Coupler (E)

Coupler (F)

Coupler (G)

Coupler (H)

Coupler (I)

Coupler (J)
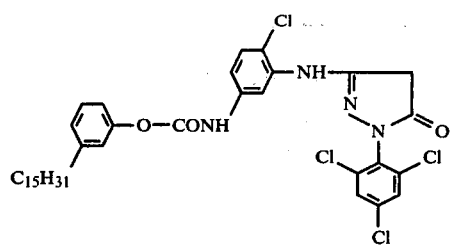
Coupler (K)
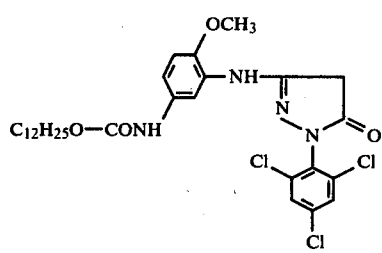
Coupler (L)
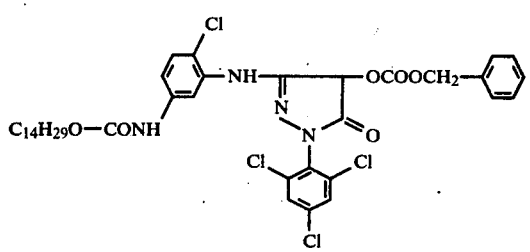
Coupler (M)
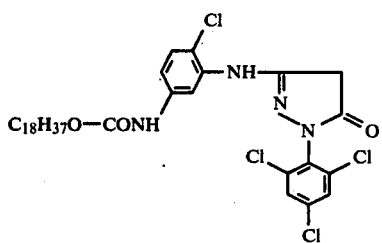
Coupler (N)
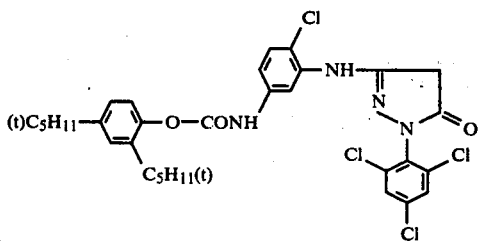
Coupler (O)
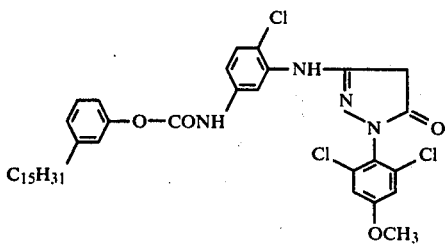
Coupler (P)
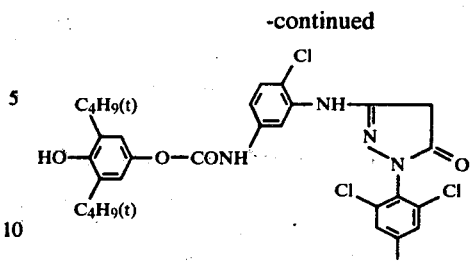
Coupler (Q)
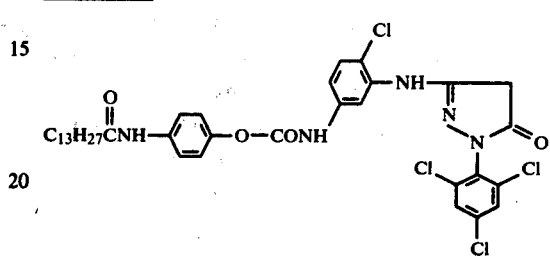
Coupler (R)
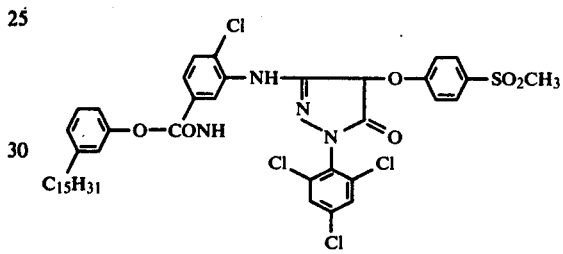
Coupler (S)
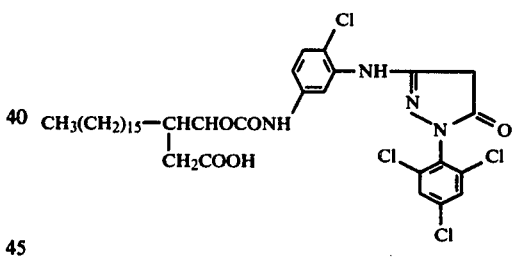
Coupler (T)
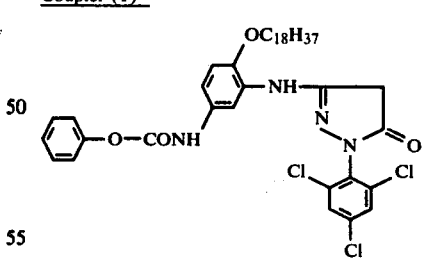
Coupler (U)
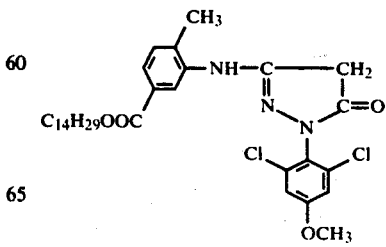
Coupler (V)

-continued

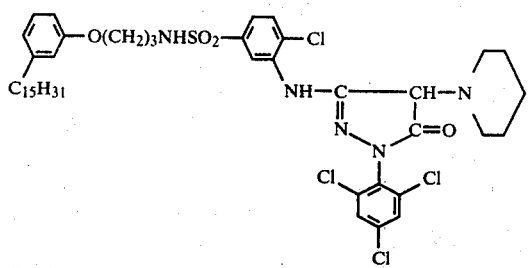

Coupler (W)

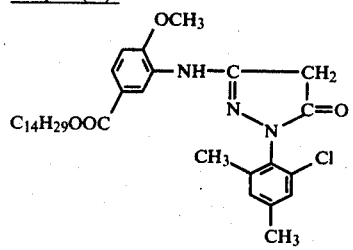

Coupler (X)

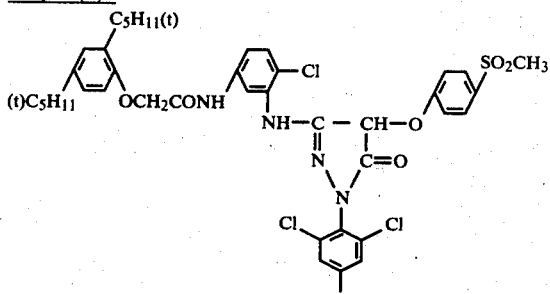

Coupler (Y)

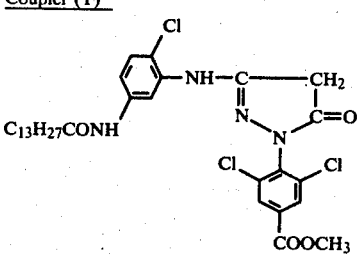

The compounds of the present invention can be added to photographic emulsions using conventional techniques for addition of couplers. Representative examples of high boiling point solvents employed for dispersing the compounds of the present invention into photographic emulsions independently or together with couplers are enumerated below. However, the present invention is not intended to be construed as being limited to these examples.

Specific examples of the high boiling point solvents include those which are described in U.S. Pat. No. 3,676,137, such as butyl phthalate, dinonyl phthalate, butyl benzoate, diethylhexyl sebacate, butyl stearate, dinonyl maleate, tributyl citrate, tricresyl phosphate, dioctylbutyl phosphate, etc.; diethyl succinate, dioctyl adipate, 3-ethylbiphenyl, liquid stabilizers for dyes which are described in "Improved Stabilizers for Photographic Dye Images" in *Products Licensing Index*, Vol. 83, pages 26–29 (March, 1971), etc.

Examples of low boiling point organic solvents which can be used as solvent assistants in combination with high boiling point organic solvents include ethyl acetate, butyl acetate, ethyl propionate, ethyl formate, butyl formate, nitromethane, carbon tetrachloride, chloroform, hexane, cyclohexane, ethylene glycol, acetone, ethanol, dimethylformamide, dioxane, etc. Further, benzene, toluene, xylene or the like can be used in a form of mixture with one of the above-described solvents.

As examples of surface active agents which are used when a solution in which the compound of the present invention is dissolved independently or together with a coupler is dispersed into an aqueous protective colloidal solution, mention may be made of saponin, and sodium alkylsulfosuccinate, sodium alkylbenzenesulfonate and so on. As examples of hydrophilic protective colloids, mention may be made of gelatin, casein, carboxymethyl cellulose, polyvinyl alcohol, polyvinyl pyrrolidone, styrene-maleic anhydride copolymer, condensate of styrene-maleic anhydride copolymer and polyvinyl alcohol, polyacrylic acid salts, ethylcellulose and so on. However, the invention is not intended to be construed as being limited to these examples.

Known magenta couplers, other than 3-anilino-5-pyrazolone couplers, can be present in emulsion layers of the present invention together with the 3-anilino-5-pyrazolone couplers. Examples of known magenta color forming couplers which can be employed in the present invention include pyrazolone compounds, indazolone compounds, cyanoacetyl compounds, etc. Particularly, pyrazolone compounds are of greater advantage than the others. Specific examples of magenta color forming couplers employable herein include those which are described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Pat. No. 1,810,464, German Patent Application (OLS) Nos. 2,408,665, 2,417,945, 2,418,959 and 2,424,467, Japanese Patent Publication Nos. 6031/65 and 45990/76, Japanese Patent Application (OPI) Ser. Nos. 20826/76, 58922/77, 129538/74, 74027/74, 159336/75, 42121/77, 74028/74, 60233/75 and 26541/76, etc.

Besides the above-described magenta couplers, the following couplers can be used in the present invention.

Yellow couplers employable in the present invention include generally closed chain ketomethylene compounds such as described in U.S. Pat. Nos. 3,341,331, 2,875,057 and 3,551,155, German Patent Application (OLS) Ser. No. 1,547,868, U.S. Pat. Nos. 3,265,506, 3,582,322 and 3,725,072, German Patent Application (OLS) Ser. No. 2,162,899, U.S. Pat. Nos. 3,369,895 and 3,408,194, German Patent Application (OLS) Ser. Nos. 2,057,941, 2,213,461, 2,219,917, 2,261,361 and 2,263,875, etc.

As cyan couplers, phenol derivatives and naphthol derivatives are suitable. Specific examples of these couplers are described in U.S. Pat. Nos. 2,369,929, 2,474,293, 2,698,794, 2,895,826, 3,311,476, 3,458,315, 3,560,212, 3,582,322, 3,591,383, 3,386,301, 2,434,272, 2,706,684, 3,034,892 and 3,583,971, German Patent Application (OLS) Ser. No. 2,163,811, Japanese Patent Publication No. 28836/70, Japanese Patent Application Ser. No. 33238/73, etc.

Couplers capable or releasing development inhibitors at the time of other color-forming reactions (so-called DIR couplers) and compounds capable of releasing compounds of this kind which have a development inhibiting action upon other color-forming reations can be also used. Examples of these couplers and compounds are described in U.S. Pat. Nos. 3,148,062, 3,227,554, 3,253,924, 3,617,291, 3,622,328 and 3,705,201, British Pat. No. 1,201,110, U.S. Pat. No. 3,297,445, 3,379,529 and 3,639,417, etc.

As examples of colored couplers employed in the present invention, mention may be made of those which are described in each of specifications of U.S. Pat. Nos. 2,434,272, 3,476,564 and 3,476,569, Japanese Patent Application Ser. No. 45971/73, U.S. Pat. Nos. 3,034,892, 3,386,301, 2,434,272, 3,148,062, 3,227,554, 3,701,783 and 3,617,291, etc.

In the introduction of the compounds (stabilizers for color images) of the present invention into photographic layers of a color sensitive material, the stabilizer for the color image may be dissolved in a low boiling point organic solvent such as ethyl acetate, ethanol, etc., and the resulting solution may be added directly to a silver halide emulsion or a mixed solution of coupler dispersions without receiving any emulsifying treatments. However, it is more desirable to first dissolve the compound of the present invention into a high boiling solvent such as dibutyl phthalate, tricresyl phosphate, etc., together with couplers and optionally, in the presence of a low boiling point solvent assistant; next disperse the resulting solution into a water-soluble protective colloid such as gelatin or the like in a state of oily droplets, and add the thus obtained emulsified dispersion lastly to a silver halide emulsion. In another process an emulsified dispersion of the present color image-stabilizing agent alone is prepared and added to a silver halide emulsion together with a coupler dispersion prepared separately.

Examples of photographic layers into which the compounds of the present invention (namely the stabilizer for color images) may be incorporated include coupler-containing silver halide light-sensitive emulsion layers (e.g., a red-sensitive silver halide emulsion layer, a green-sensitive silver halide emulsion layer and a blue-sensitive silver halide emulsion layer) and light-insensitive photographic layers (e.g., a protecting layer, a filter layer, an interlayer, a subbing layer and so on). In particular, the color image-stabilizing agent according to the present invention is incorporated in a magenta coupler-containing photographic layer, that is to say, it is particularly effective for the prevention of fading and discoloration of magenta image.

Specific examples of a support employed in the present invention include those which are usually employed in photographic sensitive materials such as a cellulose nitrate film, a cellulose acetate film, a cellulose acetate butyrate film, a cellulose acetate propionate film, a polystyrene film, a polyethylene terephthalate film, a polycarbonate film, laminates of some of these films, a thin glass film, a sheet of paper and so on. In addition, such supports as baryta paper; paper coated or laminated with an α-olefin polymer composed particularly of α-olefin monomers containing 2 to 10 carbon atoms, for example, polyethylene, polypropylene, ethylene-butene copolymer or so on; plastic films whose surfaces are improved upon the degree of contact with other macromolecular substances by roughing them according to the process described in Japanese Patent Publication No. 19068/72, and so on bring a good result.

Whether a transparent support is selected from the above-described substances or not, or whether an opaque support is selected or not depends upon the purpose or the end-use of a sensitive material. Further, supports can be rendered transparent and then colored by the addition of dyes or pigments.

Examples of opaque supports include not only naturally opaque substances such as paper but also those which are rendered opaque by adding some dye or such a pigment as titanium oxide or the like to transparent films, plastic films subjected to a surface treatment according to the process described in Japanese Patent Publication No. 19068/72, and paper, plastic films or other materials which are endowed with a perfect light-shielding ability due to the addition of carbon black or like dyes. On the support a subbing layer is usually provided. In order to effect further improvement in its adhesiveness, the surface of a support may be subjected to such a pretreatment as corona discharge, ultraviolet irradiation, flame and like treatments.

In embodiments of the present invention, to provide an ultraviolet ray absorbing layer on the top surface of photographic light-sensitive emulsion layers, which correspond to an image forming layer, in addition to the incorporation of the color image-stabilizing agent thereinto is, as a matter of course, more effective for the prevention of discoloration and fading of images caused by light.

Further, the present invention is not limited with respect to color processing agents, for example, a color developing agent, a bleaching agent, a fixing agent, etc., are used. In particular, the present invention can be applied to advantage even to low silver type color sensitive materials as described in U.S. Pat. No. 3,902,905 and so on. In addition, the present invention is not limited to the intensifier used for a color intensifying treatment described in German Patent Application (OLS) Ser. No. 181,390, Japanese Patent Application (OPI) Ser. No. 9728/73, Japanese Patent Application Ser. No. 128327/74 and so on.

Color sensitive materials to which the present invention can be applied are conventional color sensitive materials, particularly color sensitive materials for color prints. Further, the present invention may be applied to color photographic processes, particularly to a color diffusion transfer photographic process described in U.S. Pat. Nos. 3,227,550, 3,227,551 and 3,227,552, and U.S. Published Application Ser. No. B351,673, etc.

In order to produce dye images in the color photographic light-sensitive material of the present invention, color photographic developing processings are necessitated after imagewise exposure. The color photographic developing processings include basically a color development process, a bleaching process and a fixing process. In some cases, two processes are simultaneously transacted using one combined bath. In other cases, some combinations, for example, the combination of the color developing, the first fixing and the bleach-fixing processes, are feasible. Various processes, for example, a prehardening bath, a neutralizing bath, the first development (black-and-white development), an image stabilizing bath, washing with water and so on, are combined with the process for the development processing, as occasion demands. In many cases, processing temperatures above 18° C. are adopted. Temperatures ranging from 20° C. to 60° C. have been frequently selected for processing. Recently, temperatures ranging from 30° C. to 60° C. have been particularly preferred.

The color developing solution is an aqueous alkaline solution containing an aromatic primary amine color developing agent adjusted to a pH of 8 or higher, preferably 9 to 12. Specific examples of color developing agents which are preferably employed include 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfoamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfoamidoethyl-N,N-diethylaniline and the salts of these anilines (e.g., sulfates thereof, hydrochlorides thereof, sulfites thereof, p-toluenesulfonates thereof, etc.). Besides the above-described aromatic primary amines, suitable color developing agents are described in U.S. Pat. Nos. 2,193,015 and 2,592,364, Japanese Patent Application (OPI) Ser. No. 64933/73, or L. F. A. Mason, *Photographic Processing Chemistry*, pages 226–229, Focal Press, London (1966).

The color developing solution contains additionally a pH buffer such as the sulfites of alkali metals, carbonates, borates or phosphates; a development restrainer or an antifoggant such as a bromide, an iodide or an organic antifoggant; etc.

Specific examples of antifoggants include not only potassium bromide, potassium iodide and nitrobenzimidazoles described in U.S. Pat. Nos. 2,496,940 and 2,656,271, but also mercaptobenzimidazole, 5-methylbenzotriazole, 1-phenyl-5-mercaptotetrazole, such compounds as described in U.S. Pat. Nos. 3,113,864, 3,342,596, 3,295,976, 3,615,522, 3,597,199 and so on, thiosulfonyl compounds described in British Pat. No. 972,211, phenazine-N-oxides as described in Japanese Patent Publication No. 41675/71, and fog restrainers described in *Kagaku Shashin Binran* (Scientific Manual of Photography), Second Volume, pages 29–47.

In addition, the color developing solution may contain optionally a water softener; preservatives such as hydroxyl amine; organic solvents such as benzyl alcohol, diethylene glycol, etc.; a development accelerator such as polyethylene glycol, quaternary ammonium salts, amines, etc.; dye forming couplers; competing couplers; a fogging agent such as sodium borohydride, etc.; an assistant developer such as 1-phenyl-3-pyrazolidone; a viscosity endowing agent, etc.; and so on.

Conventional color development processings are conducted in the color sensitive materials of the present invention. However, color intensifying color development processings as set forth below can be also applied to the color sensitive materials of the present invention. For instance, color intensification is achieved in such a processing using peroxides, as described in U.S. Pat. Nos. 3,674,490 and 3,761,265, German Patent Application (OLS) Ser. No. 2,056,360, Japanese Patent Application (OPI) Ser. Nos. 6338/72 and 10538/72, Japanese Patent Application Ser. Nos. 89898/75, 89897/75 and 89899/75, and so on; using cobalt complex salts, as described in German Patent Application (OLS) Ser. No. 2,226,770, Japanese Patent Application (OPI) Ser. Nos. 9728/73 and 9729/73, Japanese Patent Application Ser. Nos. 76101/74, 20196/75, 57041/75, 83863/75 and 87484/75, and so on; or using chlorous acid as described in Japanese Patent Application Ser. Nos. 128327/74, 139917/74 and 27784/75 and so on.

After color development, photographic emulsion layers are usually subjected to a bleaching processing. The bleaching processing and the fixing processing may be carried out simultaneously or separately. As a bleaching agent, compounds of polyvalent metals such as Fe (III), Co (III), Cr (VI), Cu (II), etc., peroxy acids, quinones, nitroso compounds and so on are employed. More specifically, ferricyanates; dichromates; organic complex salts of Fe (III) or Co (III) such as (ethylenediaminetetraacetonato)-Fe (III) complex, (ethylenediaminetetraacetonato)-Co (III) complex, (nitrilotriacetonato)-Fe (III) or (nitrilotriacetonato)-Co (III) complex, (1,3-diamino-2-propanoltetraacetonato)-Fe (III) or (1,3-diamino-2-propanoltetraacetonato)-Co (III) complex and other aminopolycarboxylic acid complexes, citric acid complexes, tartaric acid complexes, malic acid complexes and other organic acid complexes, etc.; persulfates and permanganates; nitrosophenol; and so on can be used. Of these compounds, potassium ferricyanate, sodium (ethylenediaminetetraacetonato)-Fe (III) and ammonium (ethylenediaminetetraacetonato)-Fe (III) are particularly useful. Making an additional remark, (ethylenediaminetetraacetonato)-Fe (III) complexes are useful in both in an independent bleaching solution and a combined bleaching and fixing bath.

To the bleaching or the bleaching-fixing solutions, bleaching accelerators described in U.S. Pat. Nos. 3,042,520 and 3,241,966, Japanese Patent Publication Nos. 8506/70 and 8836/70, etc., and various additives can be also added.

The present invention will be further illustrated by the following examples.

EXAMPLE 1

The magenta coupler shown below and Compound (2) which acts as the stabilizer for a color image were dissolved in amounts of 10 g and 2 g, respectively, in a mixture of 5 ml of tricresyl phosphate and 10 ml of ethyl acetate. The resulting solution was emulsified and dispersed into an 80 g of 10% gelatin solution containing sodium dodecylbenzenesulfonate. The thus obtained emulsified dispersion was admixed with 145 g of green-sensitive silver chlorobromide (Br content: 50 mol%) emulsion (containing 7 g of silver) and thereto, sodium dodecylbenzenesulfonate was added as a coating aid. The resulting dispersion was coated on a paper support both sides of which were laminated with polyethylene films, and dried (Sample A).

Other Samples B, C, D, E, F and G were prepared in the same manner as described above except that following compounds set forth in Table 1 were used as the stabilizer for the color image, respectively.

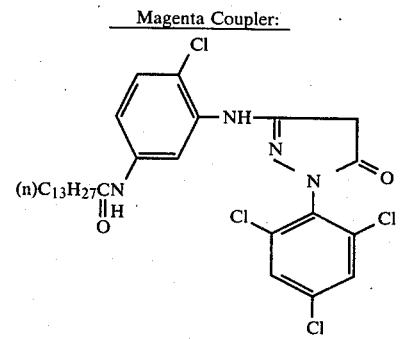

Magenta Coupler:

TABLE 1

| Sample | Stabilizer for Color Image | Amount Added | Remarks |
|---|---|---|---|
| A | Compound (2) | 2 g | Invention |
| B | Compound (15) | 2 g | Invention |

TABLE 1-continued

| Sample | Stabilizer for Color Image | Amount Added | Remarks |
|---|---|---|---|
| C | Compound (a)* | 2 g | Comparison |
| D | Compound (b)** | 2 g | Comparison |
| E | Absent | — | Comparison |
| F | Compound (2) and Compound (a) | 2 + 2 g | Invention |
| G | Compound (2) and Compound (b) | 2 + 2 g | Invention |

*Compound (a):

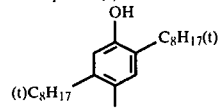

**Compound (b):

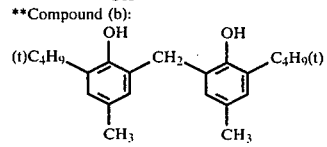

Each of these samples was exposed to light for 1 second using a sensitometer with illumination intensity of 1,000 lux and then processed with the following processing solutions:

| Composition of Developing Solution: | |
|---|---|
| Benzyl Alcohol | 15 ml |
| $Na_2SO_3$ | 5 g |
| KBr | 0.4 g |
| Hydroxylamine Sulfuric Acid Salt | 2 g |
| 4-Amino-3-methyl-N-ethyl-N-[β-(methanesulfonamido)ethyl]-p-phenylenediamine | 6 g |
| $Na_2CO_3$(monohydrate) | 30 g |
| Water to make | 1,000 ml |
| pH adjusted to | 10.1 |
| Composition of Bleaching-Fixing Solution: | |
| Ammonium Thiosulfate (70 wt %) | 150 ml |
| $Na_2SO_3$ | 15 g |
| Na[Fe(EDTA)] | 40 g |
| EDTA | 4 g |
| Water to make | 1,000 ml |
| pH adjusted to | 6.9 |

Conditions of Processings:

| Processing | temperature (°C.) | Time |
|---|---|---|
| Development | 33 | 3 min 30 sec |
| Bleach-Fixation | 33 | 1 min 30 sec |
| Washing | 28–35 | 3 min |
| Drying | | |

Each of samples in which a dye image was produced in the above-described processes underwent a fading examination under the condition that an ultraviolet ray-absorbing filter capable of cutting light having wavelengths of 400 mμ or less (a product of Fuji Photo Film Co., Ltd.) was attached to the sample, and the sample was exposed to a fluorescent lamp fadometer (intensity of illumination: 20,000 lux) for a period of 4 weeks. The results obtained are shown in Table 2.

TABLE 2

| Sample | Change in Density* of White Area | Change in** Magenta Density |
|---|---|---|
| A | +0.05 | −0.28 |
| B | +0.06 | −0.30 |
| C | +0.08 | −0.41 |
| D | +0.16 | −0.62 |
| E | +0.28 | −0.69 |
| F | +0.02 | −0.18 |

TABLE 2-continued

| Sample | Change in Density* of White Area | Change in** Magenta Density |
|---|---|---|
| G | +0.03 | −0.20 |

*White area turned yellow.
**Density before undergoing a fading test was 1.0.

EXAMPLE 2

Color sensitive materials were prepared by coating, on a paper support on both sides of which polyethylene films were laminated, in sequence the first layer (the lowest layer) to the sixth layer (the topmost layer), which are described together in Table 5. Several kinds of coating compositions for making the third layer were prepared according to the process described in Example 1, and the color sensitive materials prepared were designated H, I, J, K and L, respectively, corresponding to the kinds of color image-stabilizing agents used.

Each of these samples having thereon a green filter (SP-2) manufactured by Fuji Photo Film Co., Ltd. was exposed to light for 1 second using a sensitometer with an illumination intensity of 1,000 lux. Then, it was processed in the same manner as described in Example 1.

Each of the samples in which a dye image was produced in the above-described processes underwent a fading examination under the condition that the sample was exposed to a fluorescent lamp fadometer (intensity of illumination: 20,000 lux) for a period of 4 weeks. The results obtained are shown in Table 4.

TABLE 3

| Sample | Stabilizer | Remarks |
|---|---|---|
| H | Compound (2) | Invention |
| I | Compound (a) | Comparison |
| J | Compound (b) | Comparison |
| K | Absent | Comparison |
| L | Compound (2) and Compound (a) | Invention |

TABLE 4

| Sample | Change in Density* of White Area | Change in** Magenta Density |
|---|---|---|
| H | +0.02 | −0.11 |
| I | +0.04 | −0.28 |
| J | +0.10 | −0.35 |
| K | +0.21 | −0.49 |
| L | +0.01 | −0.08 |

*White area turned yellow.
**Density prior to a fading examination was 1.0.

TABLE 5

| Layer | Constituents and Their Contents |
|---|---|
| sixth Layer (protecting layer) | Gelatin (coated amount: 1,000 mg/m²) |
| Fifth Layer (red-sensitive layer) | Silver Chlorobromide Emulsion (Br, 50 mol %; coated amount: 300 mg of Ag/m²) Gelatin (coated amount: 1,000 mg/m²) Cyan Coupler (*1) (coated amount: 400 mg/m²) coupler solvent (*2) (coated amount: 200 mg/m²) |
| fourth Layer (interlayer) | Gelatin (coated amount: 1,200 mg/m²) Ultraviolet Absorbing Agent (*3) (coated amount: 1,000 mg/m²) solvent for Ultraviolet Absorbing Agent (*2) (coated amount: 250 mg/m²) |
| Third Layer | silver Chlorobromide Emulsion (Br, |

| Layer | Constituents and Their Contents |
|---|---|
| | 50 mol %; coated amount: 290 mg of Ag/m$^2$) |
| | Gelatin (coated amount: 1,000 mg/m$^2$) |
| | Magenta Coupler (*4) (coated amoun5: 100 mg/m$^2$) |
| | coupler Solvent (*5) (coated amount: 200 mg/m$^2$) |
| Second Layer (interlayer) | Gelatin (coated amount: 1,000 mg/m$^2$) |
| First Layer (blue-sensitive layer) | Silver Chlorobromide Emulsion (Br, 80 mol %; coated amount 400 mg of Ag/m$^2$) |
| | Gelatin (coated amount: 1,200 mg/m$^2$) |
| | Yellow coupler (*6) (coated amount: 300 mg/m$^2$) |
| | coupler Solvent (*7) (coated amount: 150 mg/m$^2$) |
| Support | Paper both sides of which are laminated with polyethylene films. |

(*1) 2-[α-(2,4 -(2,4-Di-tert-pentylphenoxy)butanamido-4,6-dichloro-5-methylphenol (cyan coupler)
(*2) Dibutyl Phthalate (solvent)
(*3) 2-(2-Hydroxy-3-sec-butyl-5-tert-butylphenyl)-benxotriazole (ultraviolet absorbing agent)
(*4) 1-(2,4,6-Trichlorophenyl)-3-(2-chloro-5-tetradecan-amido)anilino-2-pyrazolin-5-one (magenta coupler)
(*5) Tricresyl Phosphate (sovent)
(*6) α-Pivaloyl-α-(2,4-dioxo-5,5'-dimethyloxazolidin-3-yl)-2-chloro-5-[α-(2,4-di-tert-pentylphenoxy)butanzmido]-acetanilide (yellow coupler)
(*7) Dioctyl Butyl Phosphate (solvent)

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material which contains a 3-anilino-5-pyrazolone type of magenta coupler and at least one compound represented by the following formula (I):

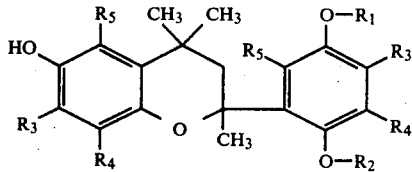

wherein $R_1$ and $R_2$ each represents a hydrogen atom, an alkyl group, a heterocyclic group, a trialkylsilyl group, an alkanesulfonyl group, an arylsulfonyl group, an aralkanesulfonyl group or a

where Y represents an alkyl group, an aryl group, an aralkyl group, an alkoxy group, an aryloxy group, an aralkyloxy group, an alkylamino group, a dialkylamino group, an arylamino group, a diarylamino group, an alkyloxycarbonyl group, an aryloxycarbonyl group, an aralkyloxycarbonyl group or an acyl group, and $R_1$ and $R_2$ may be the same or different but cannot be hydrogen atoms at the same time; and $R_3$, $R_4$ and $R_5$ each represents a hydrogen atom, an alkyl group, an alkoxy group, an aryl group, an aryloxy group, an aralkyl group, an aralkoxy group, an alkenyl group, an alkenoxy group, an acylamino group, a halogen atom, an alkylthio group, an arylthio group, a diacylamino group, an acyl group, a sulfonamido group, an alkylamino group, an alkoxycarbonyl group or an acyloxy group and $R_3$, $R_4$ and $R_5$ may be the same or different but cannot be hydrogen atoms at the same time.

2. The light-sensitive material of claim 1, wherein $R_1$ and $R_2$ each represents a hydrogen atom, a straight chain, a branched chain or a cyclic alkyl group containing 1 to 20 carbon atoms, a heterocyclic group, a trialkylsilyl group, a straight chain, a branched chain or a cyclic alkanesulfonyl group containing 1 to 20 carbon atoms, a substituted or unsubstituted arylsulfonyl group, an aralkanesulfonyl group or a

group where Y represents a straight chain, a branched chain or a cyclic alkyl group containing 1 to 20 carbon atoms, a substituted or unsubstituted aryl group, an aralkyl group, an alkoxy group whose alkyl moiety may be straight chain, branched chain or cyclic and contain 1 to 20 carbon atoms, a substituted or unsubstituted aryloxy group, an aralkyloxy group, an alkylamino group containing 1 to 20 carbon atoms, a dialkylamino group, a substituted or unsubstituted arylamino group, a diarylamino group, a straight chain, a branched chain or a cyclic alkyloxycarbonyl group containing 1 to 20 carbon atoms, a substituted or unsubstituted aryloxycarbonyl group, an aralkyloxycarbonyl group or an acyl group, and $R_1$ and $R_2$ may be the same or different but cannot be hydrogen atoms at the same time; and $R_3$, $R_4$ and $R_5$ each represents a hydrogen atom, a straight chain, a branched chain or a cyclic alkyl group containing 1 to 20 carbon atoms, a straight chain, a branched chain or a cyclic alkoxy group containing 1 to 20 carbon atoms, a substituted or unsubstituted aryl group, a substituted or unsubstituted aryloxy group, an aralkyl group, an aralkoxy group, an alkenyl group, an alkenoxy group, an acylamino group, a halogen atom, an alkylthio group whose alkyl moiety is straight chain, branched chain or cyclic and contains 1 to 20 carbon atoms, a substituted or unsubstituted arylthio group, a diacylamino group, a substituted or unsubstituted acyl group containing 1 to 20 carbon atoms, a sulfonamido group, an alkylamino group containing a straight or branched chain alkyl moiety having 1 to 20 carbon atoms, a straight or branched chain alkoxycarbonyl group containing 1 to 20 carbon atoms or an acyloxy group containing 1 to 20 carbon atoms, and $R_3$, $R_4$ and $R_5$ may be the same or different but cannot be hydrogen atoms at the same time.

3. The light-sensitive material of claim 1, wherein said magenta coupler is represented by the formula (II):

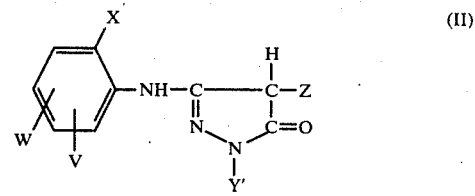

wherein X represents an alkyl group, an aryl group, an alkoxy group, an aryloxy group, an N-substituted amino group, an amido group, a halogen atom, a hydroxy group, a cyano group, or a nitro group; Y' represents a substituted or unsubstituted aryl group or a 5- or 6-membered heterocyclic group; W represents a ballast group containing 4 to 35 carbon atoms; V represents a hydrogen atom or one of the groups defined for X or W; and Z represents a hydrogen atom or a group capable of being eliminated from the coupler upon coupling reaction with an oxidized aromatic primary amine color developing agent.

4. The light-sensitive material of claim 1, wherein said compound of the formula (I) is in a magenta coupler-containing layer.

5. The light-sensitive material of claim 1, wherein said compound of the formula (I) is present in said material in an amount of about 0.5 to 200 wt% based on the weight of the magenta coupler present.

6. The light-sensitive material of claim 1, wherein said compound of the formula (I) is used in combination with a conventional fading inhibitor.

7. The light-sensitive material of claim 1, wherein said 3-anilino-5-pyrazolone coupler is used in combination with a conventional pyrazolone, indazolone, or cyanoacetyl magenta coupler.

8. The light-sensitive material of claim 1, wherein said 3-anilino-5-pyrazolone magenta coupler is used in combination with another pyrazolone magenta coupler.

* * * * *